United States Patent [19]

Korpman

[11] Patent Number: 4,759,754
[45] Date of Patent: Jul. 26, 1988

[54] SANITARY NAPKIN

[75] Inventor: Ralf Korpman, Bridgewater, N.J.

[73] Assignee: Personal Products Company, Milltown, N.J.

[21] Appl. No.: 89,781

[22] Filed: Aug. 26, 1987

[51] Int. Cl.$^4$ .............................................. A61F 13/16
[52] U.S. Cl. ..................................... 604/387; 604/389
[58] Field of Search ................ 604/387, 386, 389, 390

[56] References Cited

U.S. PATENT DOCUMENTS

| 3,676,202 | 7/1972 | Korpman . |
| 3,723,170 | 3/1973 | Korpman . |
| 3,932,328 | 1/1976 | Korpman . |
| 4,080,348 | 3/1978 | Korpman . |
| 4,285,343 | 8/1981 | McNair . |
| 4,540,415 | 9/1985 | Korpman . |
| 4,554,191 | 11/1985 | Korpman . |
| 4,608,047 | 8/1986 | Mattingly . |
| 4,701,178 | 10/1987 | Glaug et al. ............... 604/387 |

Primary Examiner—John D. Yasko

[57] ABSTRACT

A sanitary napkin having side panels intended to be folded around the crotch portion of an undergarment includes an adhesive tape tab secured to the apertured film facing of one panel with a free end overlying the opposite panel in the folded configuration. The adhesive coating on the tape tab, an A-B-A/A-B polymer having an adhesion to steel value of 75-140 oz./inch width, provides secure attachment of the tape tab while permitting detachment without substantial tearing of the aperture film facing.

10 Claims, 2 Drawing Sheets

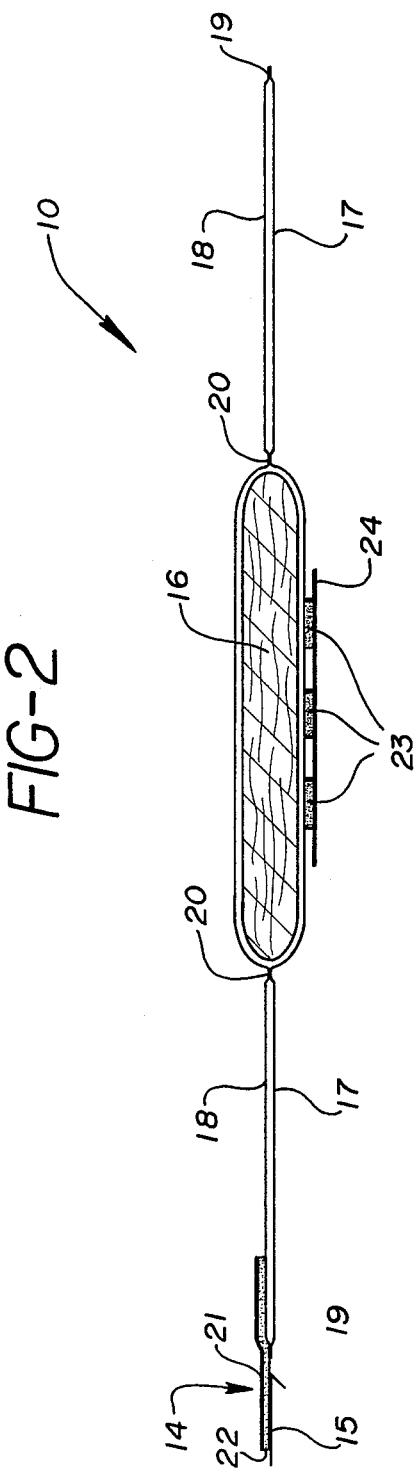

SANITARY NAPKIN

FIELD OF INVENTION

This invention relates to a sanitary napkin having side panels intended to be folded around the crotch portion of an undergarment, and more particularly to an adhesive tape tab for use in securing such side panels together in the folded position.

BACKGROUND OF THE INVENTION

Sanitary napkins having side panels intended to overly the outer crotch portion of an undergarment have been proposed as a means of improving security of attachment and protecting the edges of the garment from soiling. U.S. Pat. No. 4,608,047 discloses one such napkin wherein the side flaps overlap each other in the area in which they overly the outer crotch portion of the undergarment. In a preferred embodiment the flaps are provided with means for securing them in place such as a pressure sensitive adhesive positioned so that the flaps adhere to each other in the area where they overlap, or adhere to the outer crotch portion of the garment, or both.

U.S. Pat. No. 4,285,343 discloses a similar napkin wherein each side panel is provided with adhesive means so that when the side panels are folded over the outer surface of the undergarment each panel is adhesively secured in place. The panels may overlap so that one is secured to the other and the other is secured to the undergarment, or the panels may merely abut one another with each panel individually adhesively secured to the undergarment. The present invention is directed to a sanitary napkin having side panels wherein the panels are held in position overlying the outer crotch portion of the undergarment by a single strip of adhesive tape which is pre-attached to one panel. When the napkin is applied, the adhesive-free panel is first folded over the crotch portion of the garment followed by the second panel with the attached tape tab. The side panels and tape tab are of sufficient length to assure secure attachment of the tape tab to the opposing panel.

For convenience of application, the tape tab is applied to the liquid permeable cover of the napkin which faces to the outside when the napkin is in position. A particularly preferred napkin utilizes an apertured polyethylene film as the liquid permeable cover, and this film has presented a unique problem in connection with the adhesive tape tab. On one hand, the polyethylene film composition and the large open area requires a fairly aggressive adhesive to ensure security of attachment to the apertured film material. On the other hand, the film is very thin and tears easily due to the presence of the apertures. Thus, difficulties have been experienced in providing an adhesive composition which is effective in this use.

It is accordingly an object of the present invention to provide an improved sanitary napkin having side flaps with adhesive means for securing such side flaps around the outer crotch portion of an undergarment. It is a further object of this invention to provide a sanitary napkin having side flaps wherein the flaps are secured by means of a tape tab extending from the edge of one flap to the surface of the other. It is a still further object of this invention to provide an adhesive tape tab for securing the flaps of a sanitary napkin which provides secure attachment to an apertured film facing, and yet permits detachment without extensive tearing of such facing material. These, and other objects of this invention, will be apparent from the ensuing description and claims.

SUMMARY

The sanitary napkin of the present invention comprises, in its basic construction, an absorbent core covered on one side with a moisture impervious backing material, and on the other side with a moisture permeable apertured polymeric film. The napkin includes side flaps comprising extensions of the backing and facing materials. A tape tab secured to the facing material of one side flap extends beyond the edge of the flap, and includes a release paper to protect the otherwise exposed adhesive surface on the free end of the tape tab. The tape tab and side flaps extend to a degree sufficient so that when folded over the crotch portion of the undergarment, the free end of the tape tab extends over the surface of the opposing side flap and may be secured thereto.

The tape tab is constructed of a backing material such as film, paper or fabric, coated with an adhesive mass based on mixtures of A-B-A and A-B block copolymers formulated with a tackifying resin and having an adhesion to steel of from about 75 to 140 oz/inch width. Such adhesive compositions adhere well to the apertured polymeric film, yet release cleanly when desired without significant tearing of the film material.

DESCRIPTION OF DRAWINGS

FIG. 2 is a transverse cross-sectional view through the center of the napkin of FIG. 1 showing the construction of the napkin.

DESCRIPTION

Figure 1:
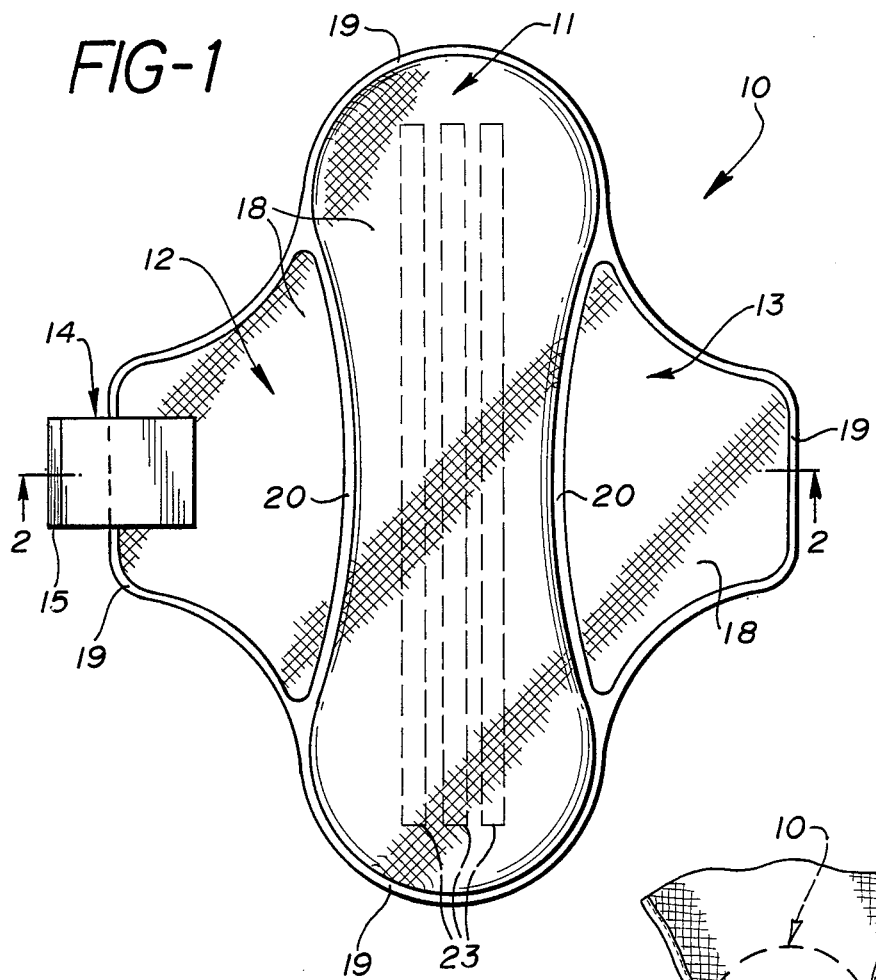
FIG. 1 is a top plan view of a sanitary napkin showing the placement of the tape tab in accordance with the present invention.

The sanitary napkin of the present invention indicated generally at 10 in FIG. 1, comprises a central elongated absorbent portion 11 which may be substantially rectangular or hourglass shaped as illustrated. Extending laterally from the longitudinal side edges of the central portion are side panels or flaps 12 and 13. Adhesively attached to panel 12 is tape tab 14 which extends beyond the edge of the panel as illustrated. The exposed adhesive surface on the free end of the tape tab is protected by a release paper 15 as best seen in FIG. 2.

The basic construction of the napkin is illustrated in the cross sectional view of FIG. 2, taken through line 2—2 of FIG. 1. Central absorbent element 16 is enclosed between backing sheet 17 and a liquid permeable facing sheet 18. The backing and facing sheets are sealed together at 19 along the outer edge of the napkin by heat seal or adhesive means. In addition, backing and facing sheets are preferably sealed together at 20 across the flap area adjacent the central absorbent element.

The absorbent element is preferably wood pulp or other conventional absorbent material known for use in sanitary napkins, The backing sheet is preferably a polymeric film, such as polyethylene, but may be any moisture impermeable material suitable for this use. The moisture permeable facing material 18, in accordance with the present invention, is a thin apertured polymeric film. The tape tab preferably comprises a substrate such as a polyester film 21 coated with adhesive mass 22 as more fully described hereinafter.

Apertured polyolefin films, particularly polypropylene and polyethylene, have been widely used as cover materials for absorbent products since these films are inexpensive, nonabsorbent and readily produced. Suitable films generally have a thickness of from about 1 to 30 mils, more preferably 3 to 10 mils, and an open area of about 30 to 60 percent. A particularly preferred material for use as a cover is a coextruded apertured film of polyethylene and ethylene vinyl acetate (EVA) as described in U.S. Pat. No. 4,690,679 wherein the film has an average open area of about 42%, a thickness of about 4.5 mils, and a weight of about 1 oz. per sq. yard. The apertures have an average equivalent diameter of about 0.016 inches and an average center-to-center spacing of about 0.028 inches. The polyethylene side of the film, which is used as the body contact side, has a higher melting point than the EVA side of the film, permitting the film to be thermally bonded while maintaining structural integrity. The outer polyethylene component of the film may be delustered with calcium carbonate while the EVA component may be pigmented with $TiO_2$ to increase the opacity of the film.

As further illustrated in FIG. 2, the afore described sanitary napkin may include one or more adhesive strips 23 on the outer surface of the central longitudinal portion of the backing material for attaching the napkin directly to the undergarment. When present, the adhesive strips are protected by release paper 24 until the napkin is ready for use. These structural elements and the materials which may be used in the sanitary napkin of the present invention are conventional for sanitary napkins and are well known in the art. Additionally, many variations in the construction and selection of materials are possible and included within the scope of the present invention.

Figure 3:
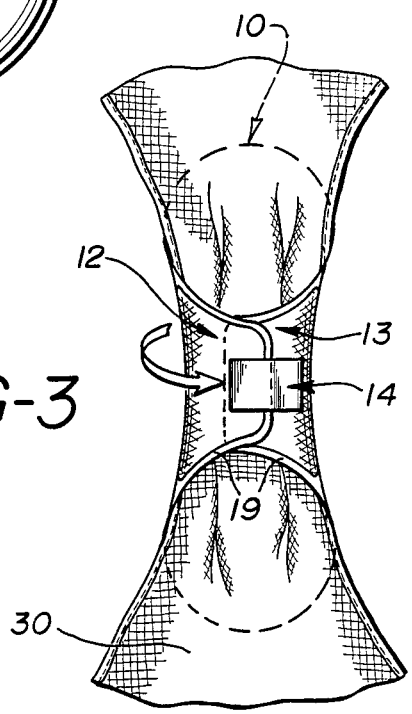
FIG. 3 is a bottom plan view of the napkin of FIG. 1 as attached to an undergarment with the side flaps folded and secured by the tape tab.

The positioning of the napkin in use is illustrated in FIG. 3 where napkin 10 is shown attached to the crotch portion of undergarment 30 with side flaps 12 and 13 folded to enclose the underside of the garment. The free end of tape tab 14, with release paper 15 having been removed, is attached to the apertured film surface of flap 13 to secure flaps 12 and 13 in their folded position. When the napkin is to be removed, tape tab 14 must be detached from the surface of flap 13, and prior to the present invention, such removal often resulted in tearing of the apertured film cover material.

Side panels 12 and 13 may overlap, abut or be spaced apart when folded around the outer surface of the undergarment. When the side panels are dimensioned so that the ends are spaced apart in the folded configuration, the tape tab must be of sufficient length to span the distance and still attach securely to the surface of the opposite panel. This configuration does have the advantage of adhering the side panels to the fabric of the undergarment as well as to each other, and thus enhances the security of the attachment of the napkin.

The adhesive mass 22 applied to the tape tab 14 in accordance with the present invention is preferably a tackified styrene-isoprene-styrene/styrene-isoprene block copolymer as disclosed in U.S. Pat. No. 4,554,191. As described therein, A-B-A block copolymers such as those disclosed in U.S. Pat. Nos. 4,136,071 and 3,676,202 can be rendered highly tacky by mixing certain combinations of A-B and A-B-A block copolymers with a high proportion of solid tackifying resin. Alternatively, the adhesive can be produced by using a styrene-isoprene-styrene copolymer which is polymerized to the correct A-B/A-B-A block ratio as is the case with Kraton 1117 (a thermoplastic elastomeric A-B-A/A-B copolymer sold by the Shell Chemical Company). The A-B-A/A-B copolymer may be tackified with a high loading of various solid tackifying resins like hydrocarbon, polyterpene or rosin esters, and may include various antioxidants and other additives. The adhesive formulation may be coated onto the substrate by extrusion, hot melt, calendar, or solvent methods.

The adhesive composition preferably comprises an elastomeric component comprising from about 25 to 85 parts by weight of a simple A-B block copolymer wherein the A blocks are derived from styrene or styrene homologues and the B blocks are derived from isoprene, and about 75 to 15 parts of an A-B-A block copolymer wherein the A and B blocks are as defined above. The A blocks in the A-B block copolymer preferably constitute about 10 to 35% by weight of the A-B copolymer and the total A-B and A-B-A copolymers preferably comprise not more than about 30% styrene. The elastomeric component is formulated with from about 100 to 150 parts of a solid tackifier, said parts being parts per 100 parts by weight of the elastomeric component. Most preferably, the adhesive layer comprises about 25 to 65 parts of the A-B copolymer, about 75 to 35 parts of the A-B-A copolymer, and about 120 to 140 parts by weight of a solid tackifier resin all per 100 parts by weight of the A-B-A/A-B elastomeric component. U.S. Pat. Nos. 3,239,478, and 2,376,202 provide a good description of the elastomeric block copolymers utilized in the present invention.

A particularly preferred formulation for adhesive layer 22 has the following formulation:

Kraton 1117: 100 parts (Kraton 1117 is a polystyrene-polyisoprene-polystyrene thermoplastic elastomer sold by the Shell Chemical Company believed to comprise about 35 parts A-B and 65 parts A-B-A).

Wingtack Plus: 120 parts (Wingtack Plus is a solid tackifier resin sold by Goodyear Tire and Rubber Company, consisting predominatly of polymerized structures derived from piperylene and isoprene with a softening point of about 95° C.)

Butyl Zimate: 2 parts (Trademark for zinc di-n-butyl-dithiocarbamate, an anti-oxidant)

Santovar A: 1 part (Trademark for 2,5-di-tert-amyl-hydroquinone, an anti-oxidant).

The substrate utilized in the adhesive tape tab of the present invention preferably comprises a plastic film, nonwoven fabric, woven fabric or paper. The preferred substrate is 1 mil polyester film.

The adhesion value of an adhesive tape is defined as that force required to strip or peel away a pressure-sensitive adhesive tape which has been secured to the surface of a clean stainless steel plate, and is quantified as oz/inch of tape width. Adhesive layer 22 preferably has an adhesion value of from about 75 to 140 oz/inch width, and preferably about 100–120 oz/inch width. This level of adhesion, combined with the tack and release properties of the A-B-A/A-B adhesive disclosed herein is found to provide secure attachment to apertured polymeric films and yet permit ready detachment without extensive tearing the film material.

From the foregoing it will be observed that the present invention is directed to an improvement in sanitary napkins having lateral side panels covered with a liquid permeable apertured film wherein the side panels are secured during use by an adhesive tape tab comprising a tackified A-B-A/A-B elastomeric copolymer adhesive formulation having an adhesion to steel value of from about 75 to 140 oz/inch width. Numerous variations and modifications of the specific embodiments described herein may be effected without departing from the true spirit and scope of the novel concept of this invention.

I claim:

1. In a sanitary napkin comprising a central elongated absorbent portion having side panels extending laterally from each longitudinal edge thereof, said absorbent portion and said side panels being covered on one side with a liquid permeable apertured polymeric film, said side panels being foldable around said central absorbent portion with said apertured polymeric film surface to the outside, the improvement comprising securing an adhesive coated tape tab to one of said side panels with a portion of said tape tab extending beyond the edge of said side panel and positioned so that when said side panels are folded around said central absorbent portion, the free end of said tape tab extends over the apertured film surface of the other of said side panels, said adhesive coating of said tape tab having an adhesion to steel value of from about 75 to 140 oz/inch width.

2. The sanitary napkin of claim 1 wherein said adhesive coating of said tape tab comprises a thermoplastic elastomeric component and a resin component, said thermoplastic elastomeric component comprising from about 25 to 85 parts of a simple A-B block copolymer wherein the A blocks are derived from styrene or styrene homologues and the B blocks are derived from isoprene, and from about 75 to 15 parts of an A-B-A block copolymer wherein the A and B blocks are as defined above, the A blocks in the A-B block copolymer constituting from about 10 to 35 percent by weight of the A-B copolymer, and the total A-B and A-B-A copolymers comprising not more than about 30% styrene, said resin component comprising from about 100 to 150 parts of a solid tackifier, all of said parts being parts per 100 parts by weight of the thermoplastic elastomeric component.

3. The sanitary napkin of claim 2 wherein said adhesive comprises about 25 to 65 parts of the A-B copolymer and about 75 to 35 parts of the A-B-A copolymer.

4. The sanitary napkin of claim 3 wherein said adhesive comprises about 120 to 140 parts by weight of a solid tackifier resin.

5. The sanitary napkin of claim 1 wherein said apertured polymeric film comprises a polyolefin film.

6. The sanitary napkin of claim 5 wherein said polyolefin film is selected from the group consisting of polypropylene, polyethylene, and bicomponent polyethylene/ethylene vinyl acetate film.

7. The sanitary napkin of claim 1 wherein said apertured film has a thickness of from 1 to 30 mils and from 30 to 60% open area.

8. The sanitary napkin of claim 7 wherein said film has a thickness of from 3 to 10 mils.

9. The sanitary napkin of claim 8 wherein said film is coextruded polyethylene/ethylene vinyl acetate having a weight of about 1 oz. per sq. yard.

10. The sanitary napkin of claim 1 wherein said adhesive has substantially the following formulation:

100 parts Kraton 1117
120 parts Wingtack Plus
2 parts Butyl Zimate
1 part Santovar A

* * * * *